United States Patent [19]

Ferrini et al.

[11] Patent Number: 4,505,913

[45] Date of Patent: Mar. 19, 1985

[54] SUBSTITUTED ANTHRANILAMIDES AND PHARMACEUTICAL PREPARATIONS CONTAINING THESE COMPOUNDS

[75] Inventors: Pier G. Ferrini, Binningen; Alberto Rossi, Oberwil; Georges Haas, Binningen, all of Switzerland

[73] Assignee: Ciba-Geigy Corporation, Ardsley, N.Y.

[21] Appl. No.: 431,456

[22] Filed: Sep. 30, 1982

Related U.S. Application Data

[63] Continuation of Ser. No. 254,232, Apr. 14, 1981, abandoned, which is a continuation of Ser. No. 061,791, Jul. 30, 1979, abandoned.

[30] Foreign Application Priority Data

Aug. 10, 1978 [CH] Switzerland ............... 8525/78

[51] Int. Cl.³ .................. A61K 31/495; C07D 241/04; C07D 401/04
[52] U.S. Cl. ...................... 514/183; 544/360; 544/379; 544/380; 544/381; 544/391; 260/239 BC; 260/244.4; 514/218; 514/255
[58] Field of Search ............... 544/380, 391; 260/239 BC, 244.4; 424/250, 244

[56] References Cited

U.S. PATENT DOCUMENTS 3,926,961 12/1975 Ferrini et al. ............ 544/391
4,182,769 1/1980 Cherkofsky et al. ......... 424/273 R

FOREIGN PATENT DOCUMENTS 439320 12/1967 Switzerland .

Primary Examiner—Glennon H. Hollrah
Assistant Examiner—James H. Turnipseed
Attorney, Agent, or Firm—Irving N. Feit

[57] ABSTRACT

Substituted anthranilamides of the formula

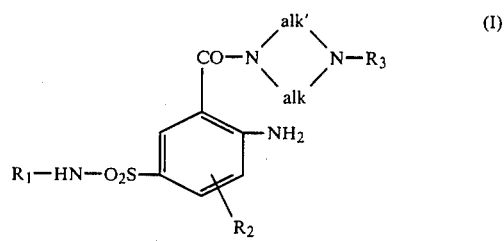

in which $R_1$ is hydrogen or an aliphatic, cycloaliphatic or cycloaliphatic-aliphatic hydrocarbon radical, $R_2$ is hydrogen, lower alkyl, lower alkoxy, halogen or trifluoromethyl, $R_3$ is hydrogen or an aliphatic or substituted or unsubstituted araliphatic or heteroaryl-aliphatic hydrocarbon radical and alk and alk' are identical or different lower alkylene radicals which separate the nitrogen atoms by 2 or 3 carbon atoms, and salts thereof, possess analgesic, anti-inflammatory and anti-allergic properties and may be used as active ingredients of analgesic, anti-inflammatory and anti-allergic pharmaceuticals. They are prepared, for example, by reacting an acid of the formula

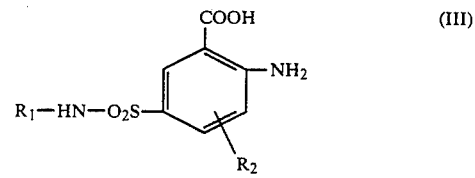

or a reactive functional derivative thereof, with an amine of the formula

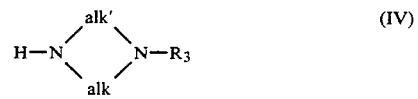

or a reactive derivative or salt thereof.

10 Claims, No Drawings

SUBSTITUTED ANTHRANILAMIDES AND PHARMACEUTICAL PREPARATIONS CONTAINING THESE COMPOUNDS

This is a continuation of application Ser. No. 254,232 filed on Apr. 14, 1981, which in turn is a continuation of application Ser. No. 061,791, filed July 30, 1979, both now abandoned.

The invention relates to novel substituted anthranilamides of the formula

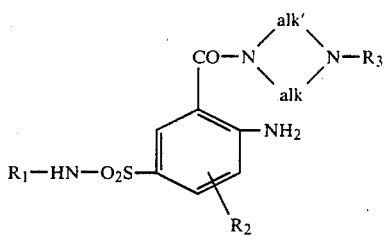

in which $R_1$ is hydrogen or an aliphatic, cycloaliphatic or cycloaliphatic-aliphatic hydrocarbon radical, $R_2$ is hydrogen, lower alkyl, lower alkoxy, halogen or trifluoromethyl, $R_3$ is hydrogen or an aliphatic or substituted or unsubstituted araliphatic or heteroaryl-aliphatic hydrocarbon radical and alk and alk' are identical or different lower alkylene radicals which separate the nitrogen atoms by 2 or 3 carbon atoms, and salts thereof, processes for their preparation, their use as medicaments and pharmaceutical preparations containing these compounds.

Aliphatic hydrocarbon radicals are, for example, lower alkyl or lower alkenyl radicals.

Cycloaliphatic hydrocarbon radicals are, for example, mono-, bi- or tri-cycloaliphatic hydrocarbon radicals. Monocycloaliphatic hydrocarbon radicals are, for example, cycloalkyl radicals having 5 to 8 ring members, such as cyclopentyl, cyclohexyl, cycloheptyl or cyclooctyl. Bicycloaliphatic hydrocarbon radicals are, for example, bicycloalkyl radicals in which the individual rings each contain 5 or 6 ring members, such as 2-bornyl, 2-norbornyl, 2-bicyclo[2.2.2]octyl or 2- or 3-bicyclo[4.4.0]decyl. Tricycloaliphatic hydrocarbon radicals are, for example, tricycloalkyl radicals in which the cycloalkyl radicals contain 5 or 6 ring members, such as 1- or 2-adamantyl.

Cycloaliphatic-aliphatic hydrocarbon radicals are, for example, those which contain one of the mono-, bi- or tri-cycloaliphatic radicals defined above, as the cycloaliphatic radical, and lower alkyl, as the aliphatic radical.

Substituted or unsubstituted araliphatic hydrocarbon radicals are, for example, phenyl-lower alkyl or phenyl-lower alkenyl radicals, which can be substituted in the phenyl moiety by lower alkyl, lower alkoxy, halogen and/or trifluoromethyl.

Substituted or unsubstituted heteroaryl-aliphatic radicals are, for example, heteroaryl-lower alkyl radicals in which the heteroaryl moiety contains 5 or 6 ring members and also an oxygen, sulfur or nitrogen atom, such as pyridyl-lower alkyl or thienyl-lower alkyl, which radicals can be substituted in the heteroaryl moiety by lower alkyl, lower alkoxy, halogen and/or trifluoromethyl.

In this specification, "lower" organic radicals and compounds are preferably understood as meaning those radicals and compounds which contain not more than 7 and in particular not more than 4 carbon atoms (C atoms).

Lower alkyl is, for example, methyl, ethyl, propyl, isopropyl, n-, sec.-, iso- or tert.-butyl or also pentyl, hexyl or heptyl.

Lower alkoxy is, for example, methoxy, ethoxy, propoxy, isopropoxy, n-, sec.-, iso- or tert.-butoxy or also pentyloxy, hexyloxy or heptyloxy.

Halogen is, for example, halogen with an atomic number of not more than 35, such as fluorine, chlorine or bromine.

Lower alkylene, which separates the nitrogen atoms in the formula I by 2 or 3 chain members, is, for example, ethylene or 1,3-propylene, or also 1,2-propylene or 1,3- or 2,3-butylene.

Lower alkenyl is, for example, vinyl, allyl or methallyl.

Phenyl-lower alkyl is, for example, benzyl, 1- or 2-phenylethyl, 1-, 2- or 3-phenylpropyl, 1- or 2-phenylisopropyl or 3- or 4-phenylbutyl.

Phenyl-lower alkenyl is, for example, 3-phenylpropen-2-yl.

Pyridyl-lower alkyl is, for example, 2-, 3- or 4-pyridylmethyl, 1- or 2-(2-, 3- or 4-pyridyl)-ethyl, 1-, 2- or 3-(2-, 3- or 4-pyridyl)-propyl, 1- or 2-(2-, 3- or 4-pyridyl)-isopropyl or 3- or 4-(2-, 3- or 4-pyridyl)-butyl.

Thienyl-lower alkyl is, for example, 2- or 3-thienyl, 1- or 2-(2- or 3-thienyl)-ethyl, 1-, 2- or 3-(2- or 3-thienyl)-propyl, 1- or 2-(2- or 3-thienyl)-isopropyl or 3- or 4-(2- or 3-thienyl)-butyl.

The compounds of the formula I have valuable pharmacological properties. In particular, they possess a pronounced antinociceptive (analgesic) action, which, for example, can be demonstrated with the aid of the acetic acid writhing syndrome in mice, in a dosage range of about 100 to 300 mg/kg administered perorally, and in rats, in a dosage range of about 10 to about 100 mg/kg administered perorally. Furthermore, they have a distinct antiinflammatory action, which can be demonstrated, for example, in rats with the aid of turpentine-induced pleuritis, in a dosage range of about 10 to about 300 mg/kg administered perorally. Further, they have a pronounced anti-allergic action, which can be demonstrated, for example, in rats with the aid of a passive cutaneous anaphylaxis, in a dosage range of 3 to about 30 mg/kg administered perorally. Accordingly, the compounds of the formula I are useful as analgesics, anti-inflammatory and/or anti-allergic agents.

The invention relates in particular to compounds of the formula I in which $R_1$ is hydrogen, lower alkyl, lower alkenyl, cycloalkyl having 5 to 8 ring members, bicycloalkyl or tricycloalkyl having 5 or 6 ring members in each ring, cycloalkyl-lower alkyl having 5 to 8 ring members or bicycloalkyl- or tricycloalkyl-lower alkyl each having 5 or 6 ring members, $R_2$ is hydrogen, lower alkyl, lower alkoxy, halogen with an atomic number of not more than 35 or trifluoromethyl, alk and alk' are identical or different lower alkylene which separates the nitrogen atoms by 2 or 3C atoms and $R_3$ is hydrogen, lower alkyl, lower alkenyl or a phenyl-lower alkyl or phenyl-lower alkenyl radical, which can be substituted in the phenyl moiety by lower alkyl, lower alkoxy, halogen and/or trifluoromethyl, or a heteroaryl-lower alkyl radical in which the heteroaryl moiety is a 5-membered or 6-membered radical which contains an oxygen, sulfur or nitrogen atom and can be substituted by lower alkyl, lower alkoxy, halogen and/or trifluoromethyl, and salts thereof.

The invention relates especially to compounds of the formula I in which $R_1$ is hydrogen, lower alkyl having not more than 4C atoms, such as methyl, ethyl, propyl, isopropyl, butyl, isobutyl or secondary butyl, lower alkenyl having not more than 4C atoms, such as allyl, cycloalkyl having 5 to 8 ring members, such as cyclopentyl, cyclohexyl or cycloheptyl, bicyclo- or tricycloalkyl having 5 or 6 ring members in each ring, such as 2-bornyl, 2-norbornyl, 2-bicyclo[2.2.2]octyl or 1- or 2-adamantyl, cycloalkenyl-lower alkyl having 5 to 8 ring members and having not more than 4C atoms in the lower alkylene moiety, such as cyclopentylmethyl, cyclohexylmethyl or cycloheptylmethyl, or bicyclo- or tricyclo-alkyl-lower alkyl having 5 or 6 ring members in each ring and having not more than 4C atoms in the lower alkylene moiety, such as 2-bornylmethyl, 2-norbornylmethyl or 2-bicyclo[2.2.2]octylmethyl, $R_2$ is hydrogen, lower alkyl having not more than 4C atoms, such as methyl, lower alkoxy having not more than 4C atoms, such as methoxy, halogen with an atomic number of not more than 35, such as chlorine, or trifluoromethyl, alk and alk' are identical or different lower alkylene which separates the nitrogen atoms by 2C atoms and has not more than 4C atoms, such as ethylene, 1,2-propylene or 2,3-butylene, and $R_3$ is hydrogen, lower alkyl having not more than 4C atoms, such as methyl, lower alkenyl having not more than 4C atoms, such as allyl, or a phenyl-lower alkyl radical which can be substituted in the phenyl moiety by lower alkyl having not more than 4C atoms, such as methyl, lower alkoxy having not more than 4C atoms, such as methoxy, halogen with an atomic number of not more than 35, such as chlorine, and/or trifluoromethyl and has not more than 4C atoms in the lower alkylene moiety, such as a benzyl, 2-phenylethyl or 3-phenylpropyl radical, a phenyl-lower alkenyl radical which can be substituted in the phenyl moiety by lower alkyl having not more than 4C atoms, such as methyl, lower alkoxy having not more than 4C atoms, such as methoxy, halogen with an atomic number of not more than 35, such as chlorine, and/or trifluoromethyl and has not more than 4C atoms in the lower alkenylene moiety, such as a 3-phenyl-propen-2-yl radical, a pyridyl-lower alkyl radical, which can be substituted in the pyridyl moiety by lower alkyl having not more than 4C atoms, such as methyl, lower alkoxy having not more than 4C atoms, such as methoxy, halogen with an atomic number of not more than 35, such as chlorine, and/or trifluoromethyl and has not more than 4C atoms in the lower alkylene moiety, such as a 2-, 3- or 4-pyridylmethyl, 2-(2-, 3- or 4-pyridyl)-ethyl or 3-(2-, 3- or 4-pyridyl)-propyl radical, or a thienyl-lower alkyl radical, which can be substituted in the thienyl moiety by lower alkyl having not more than 4C atoms, such as methyl, lower alkoxy having not more than 4C atoms, such as methoxy, halogen with an atomic number of not more than 35, such as chlorine, and/or trifluoromethyl and has not more than 4C atoms in the lower alkylene moiety, such as a 2- or 3-thienyl, 2-(2- or 3-thienyl)-ethyl or 3-(2- or 3-thienyl)-propyl radical, and salts thereof.

The invention relates in particular to compounds of the formula I in which $R_1$ is hydrogen, lower alkyl having not more than 4C atoms, such as methyl, ethyl, propyl, isopropyl, butyl, isobutyl or secondary butyl, cycloalkyl having 5 to 8 ring members, such as cyclopentyl, cyclohexyl or cycloheptyl, or tricycloalkyl having 5 or 6 ring members in each ring, such as 1- or 2-adamantyl, $R_2$ is hydrogen, lower alkyl having not more than 4C atoms, such as methyl, lower alkoxy having not more than 4C atoms, such as methoxy, halogen with an atomic number of not more than 35, such as chlorine, or trifluoromethyl, alk and alk' are identical lower alkylene which separates the nitrogen atoms by 2C atoms and has not more than 4C atoms, such as ethylene, 1,2-propylene or 2,3-butylene, and $R_3$ is hydrogen, lower alkyl having not more than 4C atoms, such as methyl, or a phenyl-lower alkyl radical which can be substituted in the phenyl moiety by lower alkyl having not more than 4C atoms, such as methyl, lower alkoxy having not more than 4C atoms, such as methoxy, halogen with an atomic number of not more than 35, such as chlorine, and/or trifluoromethyl and has not more than 4C atoms in the lower alkylene moiety, such as a benzyl, 2-phenethyl or 3-phenylpropyl radical, and salts thereof.

The invention relates very particularly to compounds of the formula I in which $R_1$ is lower alkyl having not more than 4C atoms, such as methyl, ethyl, propyl, isopropyl, butyl, secondary butyl or isobutyl, $R_2$ is hydrogen, alk and alk' are ethylene and $R_3$ is hydrogen, lower alkyl having not more than 4C atoms, such as methyl, or a phenyl-lower alkyl radical which can be substituted in the phenyl moiety by lower alkyl having not more than 4C atoms, such as methyl, lower alkoxy having not more than 4C atoms, such as methoxy, and/or halogen and has not more than 10C atoms, such as a benzyl or 2-phenethyl radical, and salts thereof.

The invention relates specifically to the compounds of the formula I which are named in the examples, and salts thereof.

The compounds of the formula I can be prepared by methods known per se.

A preferred procedure comprises effecting, in a compound of the formula

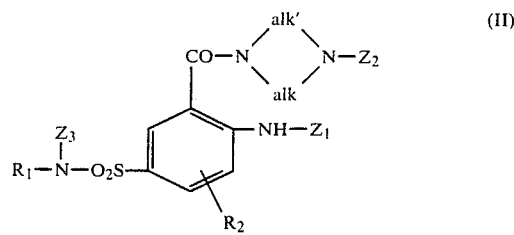

(II)

in which at least one of the radicals $Z_1$, $Z_2$ and $Z_3$ is a radical Z which is replaceable by hydrogen, and a radical $Z_1$, $Z_2$ or $Z_3$ which may differ from Z is hydrogen or, in the case of a radical $Z_2$; is a group $R_3$ which differs from hydrogen, the replacement of the radical Z by hydrogen and, if desired, converting the compound thus obtainable into another compound of the formula I and/or converting a resulting free compound into a salt or converting a resulting salt into the free compound or into another salt.

Radicals Z which are replaceable by hydrogen are, for example, radicals which are replaceable by hydrogen by reduction or solvolysis.

Radicals which are replaceable by hydrogen by reduction are, for example, substituted or unsubstituted benzyloxycarbonyl radicals, for example benzyloxy- or p-nitrobenzyloxy-carbonyl, or 2-halogeno-lower alkoxycarbonyl radicals, for example 2-iodoethoxy-, 2,2,2- trichloroethoxy- or 2,2,2-trichloro-tert.-butoxy-carbonyl. Other radicals $Z_1$ which are replaceable by hydrogen are hydroxyl and amino, which is unsubstituted or substituted by an aromatic radical, such as substituted or unsubstituted phenyl, for example anilino, and further replaceable radicals $Z_1$ and/or $Z_3$ are α-aralkyl, for example benzyl.

The replacement of the said radicals by reduction by means of hydrogen is effected in a conventional manner, for example by treatment with hydrogen in the presence of a hydrogenation catalyst, such as a nickel, platinum, rhodium, ruthenium or palladium catalyst, for example Raney nickel, platinum or platinum oxide, on charcoal if desired, a complex of rhodium chloride or ruthenium chloride and a phosphine, such as triphenylphosphine or triethylphosphine, or a palladium-on-charcoal, or if the starting materials are compounds of the formula II in which $Z_1$ is hydroxyl, a copper catalyst, for example copper-I oxide. Advantageously, the reaction is carried out in an inert solvent, such as a lower alkanol, for example in methanol or ethanol, or a lower alkanoic acid, such as acetic acid, if necessary under elevated pressure, at elevated temperature and/or in a closed vessel. 2-Halogeno-lower alkoxycarbonyl and/or hydroxyl $Z_1$ can also be replaced by hydrogen by reaction with a base metal, such as zinc, in acetic acid, or with a low valency transition metal compound, such as cobalt-II chloride, and hydroxyl groups $Z_1$ can also be replaced by hydrogen by reaction with a suitable di-(light metal) hydride, for example with lithium borohydride or sulfonated sodium borohydride.

Radicals Z which are replaceable by hydrogen by solvolysis are, for example, acyl radicals, such as acyl radicals derived from lower alkanoic acids, which can be halogenated, or from substituted or unsubstituted benzoic acid, for example formyl, acetyl, trifluoroacetyl or benzoyl, acyl radicals derived from monofunctional derivatives of carbonic acid, such as lower alkoxycarbonyl radicals, which are unsubstituted or substituted by halogen, lower alkanesulfonyl or lower alkylthio, substituted or unsubstituted benzenesulfonyl or phenylthio, or silyl radicals, for example ethoxycarbonyl, 2-iodoethoxy- or 2,2,2-trichloro-tert.-butoxy-carbonyl, 2-lower alkanesulfonyl-, 2-lower alkylthio- or 2-trimethylsilyl-ethoxycarbonyl, or substituted or unsubstituted 2-(benzenesulfonyl)- or 2-(phenylthio)-ethoxycarbonyl, for example 2-(p-toluenesulfonyl)- or 2-(p-methylphenylthio)-ethoxycarbonyl, substituted or unsubstituted benzyloxycarbonyl radicals, for example benzyloxycarbonyl or p-nitrobenzyloxycarbonyl, cycloalkoxycarbonyl radicals, for example isobornyloxycarbonyl, or halogenocarbonyl, for example chlorocarbonyl, and also cyano or silyl radicals, such as trimethylsilyl. Further radicals $Z_1$ which are replaceable by hydrogen by solvolysis are hydrocarbon radicals which contain a hydroxyl substituent in the α-position and can be further substituted, such as α-hydroxylower alkyl, for example 1-hydroxyethyl or 2-(2-hydroxy)-propyl, α-hydroxycycloalkyl radicals, such as 1-hydroxycyclohexyl, or substituted or unsubstituted α-hydroxyphenyl-lower alkyl radicals, such as α-hydroxy-benzyl radicals.

The replacement of the said solvolysable groups Z by hydrogen by means of solvolysis is effected in a conventional manner, for example by hydrolysis, if necessary in the presence of an acid or basic hydrolysing agent and/or of a solvent, preferably a water-miscible solvent, such as a lower alkanol, for example ethanol, a di-lower alkyl ketone, for example acetone, or a lower alkanoic acid amide, for example dimethylformamide, and/or at elevated temperature. Acid hydrolysing agents are, for example, proton acids, such as mineral acids, for example hydrochloric acid, sulfuric acid or phosphoric acid, or organic carboxylic acids, such as lower alkanoic acids, which can be halogenated, for example formic acid, acetic acid or chloroacetic or trichloroacetic acid. Basic hydrolysing agents are, for example, alkali metal hydroxides or alkaline earth metal hydroxides, such as sodium hydroxide, potassium hydroxide or calcium hydroxide, alkali metal carbonates, such as sodium carbonate or potassium carbonate, ammonia or organic nitrogen bases, such as tribenzyl-methyl-ammonium hydroxide. Tertiary lower alkoxycarbonyl groups, such as tert.-butoxycarbonyl, can also be replaced by hydrogen by solvolysis under anhydrous conditions by reaction with a suitable carboxylic acid, such as trifluoroacetic acid, and silyl and 2-silylethoxycarbonyl groups can be replaced by hydrogen by solvolysis under anhydrous conditions by reaction with a salt of hydrofluoric acid, for example with potassium fluoride in acetonitrile.

The starting materials of the formula II can be prepared by methods known per se, for example by reacting an acid of the formula

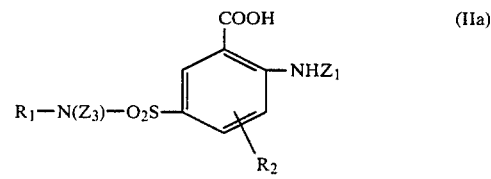

or a reactive functional derivative thereof, with an amine of the formula

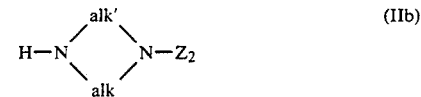

or a reactive derivative or salt thereof, for example by reacting a 5-($R_1$-sulfamoyl)-N-$Z_1$-anthranilic acid with the N-chlorocarbonyl derivative or a N-lower alkane-, such as N-methane-, or N-benzenesulfenic acid derivative of a compound of the formula IIb, or by reacting a 5-($R_1$-sulfamoyl)-isatoic anhydride with a compound of the formula IIb in which $Z_2$ is a radical Z. The reaction is carried out in a conventional manner, especially as indicated below for the reaction of compounds of the formulae III and IV or their reactive derivatives.

Starting materials of the formula II in which $Z_1$ is hydroxyl, as the radical which is replaceable by hydrogen by reduction, are advantageously prepared in situ under the reducing conditions, by reduction of the corresponding 5-($R_1$-sulfamoyl)-2-nitro-benzoic acid amides, or salts thereof. The latter compounds, in turn, are accessible by reacting corresponding 5-(chlorosulfonyl)-2-nitrobenzoic acids with a compound of the formula $R_1$—$NH_2$, converting the 5-($R_1$-sulfamoyl)-2-nitrobenzoic acid thus obtainable into a reactive derivative if desired, for example converting it to the acid chloride using thionyl chloride, and subsequently carrying out a conventional condensation reaction with the amine of the formula IIb or a reactive derivative or salt thereof. Compounds of the formula II in which $Z_1$ is a hydrocarbon radical substituted in the α-position by hydroxyl are prepared analogously in situ, advantageously by acid hydrolysis of the corresponding 5-($R_1$-sulfamoyl)-anthranilic acid amides, which are substituted on the anilino N atom by a divalent hydrocarbon radical, which can be substituted. The latter compounds are obtained, for example, by reacting the corresponding 5-chlorosulfonyl-2-chloro-benzoic acids with an amine $R_1$—$NH_2$, then subjecting the product to ammonolysis and subjecting the 5-($R_1$-sulfamoyl)-anthranilic acid, which is thus obtainable, to a condensation reaction with α-oxohydrocarbons, for example benzaldehyde or acetaldehyde, converting the product to the chloride and reacting the 5-($R_1$-sulfamoyl)-anthraniloyl chloride which is substituted on the anilino N atom and is thus obtainable, for example 5-($R_1$-sulfamoyl)-2-benzylideneamino-benzoyl chloride, with a compound of the formula IIb.

The compounds of the formula I can also be prepared by reacting an acid of the formula

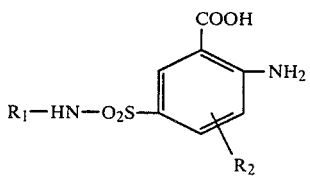  (III)

or a reactive functional derivative thereof, with an amine of the formula

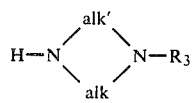  (IV)

or a reactive derivative or salt thereof, and, if desired, converting the compound thus obtainable into another compound of the formula I and/or converting a resulting free compound into a salt and/or converting a resulting salt into the free compound or into another salt.

Reactive functional derivatives of acids of the formula III are, for example, reactive esters, such as substituted or unsubstituted phenyl esters, for example phenyl, p-nitrophenyl or 2,4-dinitrophenyl esters, reactive amides, such as 1-imidazolides, or anhydrides thereof, such as open-chain anhydrides with a mineral acid, for example acid chlorides, anhydrides with phosphinous or phosphorous acids, for example with diphenylphosphinous acid, or with carbonic acid half-esters or acid phosphorous acid esters, such as carbonic acid monophenyl ester or carbonic acid monoethyl ester or diethyl phosphite, or cyclic anhydrides thereof, such as compounds of the formula

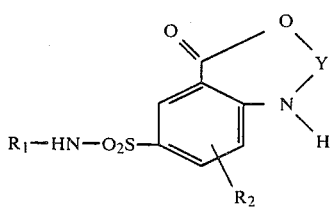  (IIIa)

in which Y is a carbonyl, thiocarbonyl or sulfinyl group or a group of the formulae

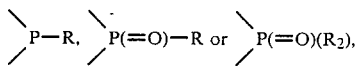

in which R is an organic radical, such as lower alkyl, for example methyl, or substituted or unsubstituted phenyl.

Reactive derivatives of compounds of the formula IV are, for example, their acyl derivatives derived from half-esters of carbonic acid or halogenoformic acid, such as lower alkoxycarbonyl or halogenocarbonyl, for example chlorocarbonyl derivatives, or sulfenylamides thereof with organic sulfenic acids, such as lower alkanesulfenic acids, or substituted or unsubstituted benzenesulfenic acids, for example with methanesulfenic acid or benzenesulfenic acid.

The reaction of compounds of the formulae III and IV or of reactive derivatives thereof is carried out in the manner customary for the particular reaction.

When reacting acids of the formula III with amines of the formula IV or the salts thereof, the reaction is advantageously carried out in the presence of a waterbinding agent, preferably of phosphorus pentoxide or of an ester of pyrophosphorous acid, for example of tetraethyl pyrophosphite, or with removal of the water of reaction by distillation, preferably azeotropic distillation, and if necessary in an inert solvent, such as toluene, and/or at elevated temperature, for example at about 50° to 200° C.

The reaction of reactive esters or amides or of anhydrides of acids of the formula III with amines of the formula IV or the salts thereof is advantageously carried out in a solvent which is inert towards the reactants, for example in toluene, xylene, tetrahydrofuran or dioxan, and if necessary in the presence of a basic condensing agent, such as a tertiary organic nitrogen base, such as triethylamine or pyridine, and/or at a lowered or elevated temperature, for example in the temperature range of about 0° to about 150°.

The reaction of acids of the formula III with acyl derivatives of amines of the formula IV is preferably carried out with heating, for example at about 100° to 250° C., and if necessary in a solvent which is inert towards the reactants, such as xylene, whilst the reaction with sulfenylamides derived from amines of the formula IV is preferably carried out at normal temperature, for example at about 0° to 50° C., and preferably in an inert solvent, such as a N,N-di-lower alkylamide, for example dimethylformamide, or N-methylpyrrolidone, in pyridine, in an ether, for example diethyl ether, dioxan or tetrahydrofuran, or in benzene, toluene or xylene.

The starting materials of the formula III and IV can be prepared in a manner known per se.

Acids of the formula III are obtained, for example, by reacting a corresponding 5-chlorosulfonyl-2-chlorobenzoic acid with an amine $R_1$—$NH_2$ and subjecting the resulting 5-($R_1$-sulfamoyl)-2-chloro-benzoic acid to ammonolysis in a conventional manner.

Reactive esters of acids of the formula III are obtained, for example, by conventional esterification, such as by reaction with the corresponding alcohol in the presence of a mineral acid, such as sulfuric acid or hydrochloric acid.

Reactive amides of acids of the formula III can be obtained, for example, by reacting the acid in a conventional manner with a corresponding urea, such as bis(1-imidazolyl)-urea, with a dihalide, diester or esterhalide of carbonic acid, such as lower alkyl halogenoformate, with an ester or halide of a phosphinous acid of the formula $(R)_2P$—OH, such as a lower alkyl ester, for example the ethyl ester, of benzenephosphinous acid or benzenephosphinous acid chloride, a diester, esterhalide or dihalide of a phosphonous acid of the formula R—P(OH)$_2$, for example benzenephosphonous acid dichloride, or a diester, ester-halide or halide of a phosphonic acid of the formula R—P(=O)(OH)$_2$, for example benzenephosphonic acid dichloride. Isatoic anhydrides of the formula III in which Y is carbonyl are advantageously prepared by reacting 5-chlorosulfonylisatoic acid with an amine of the formula $R_1$—NH$_2$ in a conventional manner.

Open-chain anhydrides of acids of the formula III are advantageously formed in situ under the reaction conditions, by reacting the corresponding acid with, for example, a halogenating agent, such as thionyl chloride, or with an ester or halide of a phosphinous acid or an ester, ester-halide or dihalide of a phosphonous acid or phosphonic acid, for example with benzenephosphinous acid chloride, benzenephosphinous acid ethyl ester or benzenephosphonous or benzenephosphonic acid dichloride, ethyl ester-chloride or diethyl ester.

Reactive derivatives of amines of the formula IV are likewise advantageously produced in situ under the reaction conditions, by reacting the amine with a halogenoformic acid ester or in the presence of a trivalent phosphorus compound, for example triphenylphosphine, with an organic disulfide, for example a di-lower alkyl disulfide.

Compounds obtainable according to the invention can be converted to other compounds of the formula I.

Thus, in compounds of the formula I in which $R_3$ is hydrogen, a radical $R_3$ which differs from hydrogen can be introduced. The introduction of the radical $R_3$ is effected in a conventional manner, for example by reaction with a reactive ester of an aliphatic or substituted or unsubstituted araliphatic or heteroaryl-aliphatic alcohol, such as an ester thereof with an organic sulfonic acid, such as with benzenesulfonic acid, p-bromobenzenesulfonic acid, toluenesulfonic acid or methanesulfonic acid, or with an inorganic sulfonic acid, such as with fluorosulfonic acid, or with a mineral acid, such as with hydrochloric acid, hydrobromic acid or hydriodic acid or sulfuric acid.

The reaction is preferably carried out in the presence of an acid-binding agent, such as a tertiary organic base, for example ethyldiisopropylamine, pyridine or quinoline, or an inorganic base, such as an alkali metal hydroxide or alkaline earth metal hydroxide or an alkali metal carbonate, for example sodium hydroxide, potassium hydroxide or calcium hydroxide, or potassium carbonate or sodium carbonate. Preferably, the reactions described are carried out in an inert organic solvent, such as an alkanol, for example in ethanol or methanol, or a hydrocarbon, for example in benzene, toluene or xylene, an ether, such as diethyl ether, tetrahydrofuran or dioxan, or a chlorinated or nitrated hydrocarbon, for example in methylene chloride, carbon tetrachloride, nitrobenzene or nitromethane.

However, the introduction of a radical $R_3$ can also be effected by reaction with a corresponding oxo compound, for example with a corresponding aldehyde or ketone under reducing conditions, for example in the presence of hydrogen in the presence of a hydrogenation catalyst, such as a palladium, platinum or nickel catalyst, for example palladium-on-charcoal or palladium-on-calcium carbonate, or platinum oxide or Raney nickel, under normal pressure or preferably under elevated pressure, or in the presence of an organic reducing agent, such as formic acid or formaldehyde, if desired in aqueous solution, in which case the reaction is preferably carried out at elevated temperature, or in the presence of a di-(light metal) hydride, for example diisoamyl borohydride, such as sodium cyanoborohydride or sodium borohydride, in each case advantageously in a solvent which is inert under the reaction conditions.

Conversely, in compounds of the formula I in which $R_3$ differs from hydrogen, $R_3$ can be replaced by hydrogen, for example by reaction with a halogenoformic acid ester, such as a lower alkyl chloroformate or bromoformate, or a cyanogen halide, such as cyanogen bromide or cyanogen chloride, with the formation of the corresponding urethane or cyanamide, and subsequent hydrolysis of the latter. α-Aralkyl radicals and α-heteroarylalkyl radicals $R_3$ can also be replaced by hydrogen by reduction, for example by treatment with hydrogen in the presence of a hydrogenation catalyst, such as palladium-on-charcoal.

Furthermore, in compounds of the formula I in which $R_2$ is hydrogen, radicals $R_2$ which differ from hydrogen can be introduced. Thus, halogen can be introduced in a conventional manner, for example by reaction with chlorine or bromine, preferably in the presence of a catalyst, such as iron-III chloride, or with N-chlorosuccinimide. Furthermore, trifluoromethyl can be introduced in a conventional manner, for example by reaction with trifluoroiodomethane in the presence of metals, such as copper powder. Furthermore, lower alkyl can be introduced in a conventional manner, for example by reaction with a lower alkyl halide, advantageously in the presence of a catalyst, such as a metal halide, for example aluminium chloride or aluminium bromide.

The said reactions can, if desired, be carried out at the same time or successively and in any order.

The said reactions are carried out in a conventional manner in the presence or absence of diluents, condensing agents and/or catalytic agents, at lowered, normal or elevated temperature and if necessary in a closed vessel.

Depending on the process conditions and starting materials, the end products are obtained in the free form or in the form of their acid addition salts, which is also included in the invention.

These acid addition salts are in particular pharmaceutically usable acid addition salts, such as corresponding mineral acid salts, for example hydrochlorides, hydrobromides or hydroiodides, sulfates, hydrogen sulfates or phosphates, or corresponding carboxylic acid salts, such as fumarates, maleates, citrates, anthranilates, p-hydroxybenzoates, pyruvates or salicylates, and also corresponding sulfonic acid salts, such as cyclohexylaminesulfonates, sulfanilates or p-toluenesulfonates. Thus, for example, basic, neutral or mixed salts, and in some cases also hemihydrates, monohydrates, sesquihydrates or polyhydrates thereof, can be obtained. The acid addition salts of the novel compounds can be converted to the free compound in a manner known per se, for example by means of basic agents, such as alkalis or ion exchangers. On the other hand, the resulting free bases can form salts with organic or inorganic acids.

The salts of the novel compounds, for example the picrates, can also be used to purify the resulting free bases, by converting the free bases into salts, separating these off and liberating the bases from the salts again. Because of the close relationship between the novel compounds in the free form and in the form of their salts, what is stated in this specification in respect of the free compounds also applies by analogy to the corresponding salts.

The invention also relates to those embodiments of the process in which a compound obtainable as an intermediate at any process stage is used as the starting material and the missing process steps are carried out, or in which a starting material is formed under the reaction conditions or is used in the form of a derivative thereof, if desired in the form of a salt.

The starting materials used in the process of the present invention are preferably those which result in the compounds described initially as being particularly valuable. Novel starting materials and processes for their preparation are also a subject of the present invention.

The pharmaceutical preparations according to the invention, which contain compounds of the formula I or pharmaceutically usable salts thereof, are those which are intended for enteral, such as oral or rectal, and parenteral administration and for topical application to warm-blooded animals and which contain the pharmacological active ingredient on its own or together with a pharmaceutically usable carrier. The dosage of the active ingredient depends on the species of warm-blooded animal, on the age and on the individual condition, and also on the mode of administration. In the normal case, an approximate daily dose of about 15-300 mg, advantageously divided into several identical partial doses, is to be proposed for a warm-blooded animal weighing about 75 kg, in the case of oral administration.

The novel pharmaceutical preparations contain, for example, from about 10% to about 80% and preferably from about 20% to about 60% of the active ingredient. Pharmaceutical preparations, according to the invention, for enteral or parenteral administration are, for example, those in dosage unit forms, such as sugar-coated tablets, tablets, capsules or suppositories, and also ampoules. These are prepared in a manner known per se, for example by conventional mixing, granulating, sugar-coating, dissolving or lyophilising methods. Thus, pharmaceutical preparations for oral use can be obtained by combining the active ingredient with solid carriers, granulating a resulting mixture if desired and processing the mixture or granules, after the addition of suitable adjuncts if desired or necessary, to tablets or sugar-coated tablet cores.

Suitable carriers are in particular fillers, such as sugars, for example lactose, sucrose, mannitol or sorbitol, cellulose preparations and/or calcium phosphates, for example tricalcium phosphate or calcium hydrogen phosphate, and also binders, such as starch paste, for example maize, corn, rice or potato starch paste, gelatin, tragacanth, methylcellulose and/or polyvinylpyrrolidone, and/or, if desired, disintegrators, such as the above starches, and also carboxymethyl starch, cross-linked polyvinylpyrrolidone, agar or alginic acid or a salt thereof, such as sodium alginate. Adjuncts are in particular glidants and lubricants, for example silicic acid, talc, stearic acid or salts thereof, such as magnesium stearate or calcium stearate, and/or polyethylene glycol. Sugar-coated tablet cores are provided with suitable coatings which can be resistant to gastric juices, using, inter alia, concentrated sugar solutions which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or the coatings of sugar-coated tablets, for example to identify or indicate different doses of active ingredient.

Further pharmaceutical preparations for oral administration are dry-filled capsules made of gelatin, and also soft, sealed capsules made of gelatin and a plasticiser, such as glycerin or sorbitol. The dry-filled capsules can contain the active ingredient in the form of granules, for example in admixture with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers can also be added.

Suitable pharmaceutical preparations for rectal administration are, for example, suppositories, which consist of a combination of the active ingredient with a suppository base. Examples of suitable suppository bases are natural or synthetic triglycerides, paraffin hydrocarbons, polyethylene glycols or higher alkanols. Furthermore, gelatin rectal capsules, which contain a combination of the active ingredient with a base, can also be used; suitable base materials are, for example, liquid triglycerides, polyethylene glycols or paraffin hydrocarbons.

Preparations suitable for parenteral administration are, in particular, aqueous solutions of an active ingredient in a water-soluble form, for example aqueous solutions of a water-soluble salt, and also suspensions of the active ingredient, such as corresponding oily injection suspensions, for which suitable lipophilic solvents or vehicles are used, such as fatty oils, for example sesame oil, or synthetic fatty acid esters, for example ethyl oleate or triglycerides, or aqueous injection suspensions, which contain substances which increase the viscosity, for example sodium carboxymethylcellulose, sorbitol and/or dextran, and can also contain stabilisers.

Pharmaceutical preparations for topical application are, in particular, creams, ointments, pastes, foams, tinctures and solutions, which contain from about 0.5 to about 20% of the active ingredient.

The present invention also relates to the use of the compounds of the formula I and of the salts of such compounds having salt-forming properties, preferably for the treatment of inflammations and in particular for the treatment of inflammatory chronic diseases of the rheumatic type, especially chronic arthritis.

The following examples illustrate the present invention without in any way restricting the scope thereof. Temperatures are in degrees centigrade.

EXAMPLE 1

2.7 g of 1-methylpiperazine are added slowly to a suspension of 10.2 g of 5-[N-(1-adamantyl)-sulfamoyl]-isatoic anhydride in 250 ml of absolute toluene, at 100° with stirring. After the addition is ended, the mixture is stirred for a further 1 hour at 100° and is allowed to cool to room temperature, the precipitate is separated off by decanting and the crude product thus obtained is recrystallised from ethanol. 5-[N-(1-Adamantyl)-sulfamoyl]-anthranilic acid (4-methyl)-piperazide with a melting point of 214°-215° is obtained. (Melting point of the hydrochloride: 298°-300°).

The starting material can be obtained, for example, as follows:

30.5 g of 2-chloro-5-chlorosulfonyl-benzoic acid are added in portions to 165 ml of water and 36.1 g of 1-amino-adamantane, with stirring, at room temperature, and the mixture is stirred for a further 1 hour, acidified to pH 1 with concentrated hydrochloric acid and filtered. This yields 5-[N-(1-adamantyl)-sulfamoyl]-2-chloro-benzoic acid with a melting point of 207°-210°.

350 ml of 25% aqueous ammonia solution and 1 g of copper powder are added to 16.9 g of this compound and the mixture is heated at 125°-130° for 12 hours in an autoclave. It is then cooled to room temperature and filtered through silica gel, the filtrate is acidified to pH 5 with concentrated hydrochloric acid and allowed to stand overnight at 0° and the crystals formed are filtered off. This yields 5-[N-(1-adamantyl)-sulfamoyl]-anthranilic acid with a melting point of 168°-171° (decomposition).

A suspension of 14.2 g of the above compound in 140 ml of acetic acid is warmed at 70° for 10 minutes, with stirring. It is then cooled to room temperature and phosgene is passed in until the mixture is saturated. The customary safety measures must be taken during this step. The mixture is then warmed at 100° for 20 minutes. It is then cooled to room temperature, a little water is added, the precipitate which separates out immediately is filtered off with suction and washed successively with water and diethyl ether and the crystalline product is dried in vacuo at 100°. 5-[N-(1-Adamantyl)-sulfamoyl]-isatoic anhydride with a melting point of 164° (decomposition) is thus obtained.

EXAMPLE 2

In a manner analogous to that described in Example 1, the reaction of 5-[N-(2-butyl)-sulfamoyl]-isatoic anhydride with 1-methylpiperazine yields 5-[N-(2-butyl)-sulfamoyl]-anthranilic acid (4-methyl)-piperazide with a melting point of 130°-132° (from an ethanol/diethyl ether mixture). The hydrochloride melts at 246°-248°.

5-[N-(2-Butyl)-sulfamoyl]-isatoic anhydride, which is to be used as the starting material, can be obtained, for example, in a manner analogous to that described in Example 1, using 2-chloro-5-chlorosulfonylbenzoic acid as the starting material, the product being obtained via 5-[N-(2-butyl)-sulfamoyl]-2-chloro-benzoic acid with a melting point of 118°-123° and 5-[N-(2-butyl)-sulfamoyl]-anthranilic acid with a melting point of 187°-188°. It melts at 228°-229°.

EXAMPLE 3

In a manner analogous to that described in Example 1, the reaction of 5-(N-cyclohexylsulfamoyl)-isatoic anhydride with 1-methylpiperazine yields 5-(N-cyclohexylsulfamoyl)-anthranilic acid (4-methyl)-piperazide with a melting point of 167°-168° (from ethanol). The hydrochloride melts at 263°-264°.

5-(N-Cyclohexylsulfamoyl)-isatoic anhydride, which is to be used as the starting material, can be obtained, for example, in a manner analogous to that described in Example 1, using 2-chloro-5-chlorosulfonylbenzoic acid as the starting material, the product being obtained via 2-chloro-5-(N-cyclohexylsulfamoyl)-benzoic acid with a melting point of 168°-175° and 5-(N-cyclohexylsulfamoyl)-anthranilic acid with a melting point of 204°-206°. It melts at 232°-233°.

EXAMPLE 4

In a manner analogous to that described in Example 1, the reaction of 5-[N-(2-methylpropyl)-sulfamoyl]-isatoic anhydride with 1-methylpiperazine yields 5-[N-(2-methylpropyl)-sulfamoyl]-anthranilic acid (4-methyl)-piperazide with a melting point of 162°-163° (from ethanol; melting point of the hydrochloride: 254°-255°).

5-[N-(2-Methylpropyl)-sulfamoyl]-isatoic anhydride, which is to be used as the starting material, can be obtained, for example, in a manner analogous to that described in Example 1, using 2-chloro-5-chlorosulfonyl-benzoic acid as the starting material, the product being obtained via 2-chloro-5-[N-(2-methylpropyl)-sulfamoyl]-benzoic acid with a melting point of 163°-166° and 5-[N-(2-methylpropyl)-sulfamoyl]-anthranilic acid with a melting point of 203°-205°; the product melts at 270°-273°.

EXAMPLE 5

In a manner analogous to that described in Example 1, the reaction of 5-(N-isopropylsulfamoyl)-isatoic anhydride with 1-methylpiperazine yields 5-(N-isopropylsulfamoyl)-anthranilic acid (4-methyl)-piperazide with a melting point of 118°-122° (from methylene chloride/diethyl ether; melting point of the methanesulfonate: 232°-234°).

5-(N-Isopropylsulfamoyl)-isatoic anhydride, which is to be used as the starting material, can be obtained, for example, in a manner analogous to that described in Example 1, using 2-chloro-5-chlorosulfonyl-benzoic acid as the starting material, the product being obtained via 2-chloro-5-(N-isopropylsulfamoyl)-benzoic acid with a melting point of 170°-173° and 5-(N-isopropylsulfamoyl)-anthranilic acid with a melting point of 230°-232°; the product melts at 235°-237°.

EXAMPLE 6

In a manner analogous to that described in Example 1, the reaction of 5-(N-methylsulfamoyl)-isatoic anhydride with 1-methylpiperazine yields 5-(N-methylsulfamoyl)-anthranilic acid (4-methyl)-piperazide in the form of an oil (melting point of the methanesulfonate: 120°-123°).

5-(N-Methylsulfamoyl)-isatoic anhydride, which is to be used as the starting material, can be obtained, for example, in a manner analogous to that described in Example 1, using 2-chloro-5-chlorosulfonyl-benzoic acid as the starting material, the product being obtained via 2-chloro-5-(N-methylsulfamoyl)-benzoic acid with a melting point of 170°-172° and 5-(N-methylsulfamoyl)-anthranilic acid with a melting point of 205°; the product melts at 260°.

EXAMPLE 7

In a manner analogous to that described in Example 1, the reaction of 5-(N-ethylsulfamoyl)-isatoic anhydride with 1-methylpiperazine yields 5-(N-ethylsulfamoyl)-anthranilic acid (4-methyl)-piperazide with a melting point of 175°-177° (from acetone/ethanol).

5-(N-Ethylsulfamoyl)-isatoic anhydride, which is to be used as the starting material, can be obtained, for example, in a manner analogous to that described in Example 1, using 2-chloro-5-chlorosulfonyl-benzoic acid as the starting material, the product being obtained via 5-(N-ethylsulfamoyl)-2-chloro-benzoic acid with a melting point of 186°–190° and 5-(N-ethylsulfamoyl)-anthranilic acid with a melting point of 190°–192°; the product melts at 253°–255°.

EXAMPLE 8

99 g of 5-methylsulfamoylisatoic anhydride are suspended in 1,100 ml of dioxan, the suspension is warmed to 90° and 81 g of N-[2-(p-chlorophenyl)-ethyl]-piperazine, dissolved in 1,100 ml of dioxan, are added dropwise in the course of 180 minutes. The reaction mixture is warmed at 90° until the evolution of gas has ceased, allowed to cool and filtered and the filtrate is evaporated. The evaporation residue is dissolved in acetone and the solution is filtered through about 1,300 g of silica gel (0.06–0.2 mm). After 600 ml of first runnings, the eluates are combined and evaporated and the residue is dried. This yields 5-(N-methylsulfamoyl)-anthranilic acid 4-[2-(p-chlorophenyl)-ethyl]-piperazide. This can be converted to the fumarate with a melting point of 224°–226° by dissolving in 2,000 ml of methanol, adding a solution of 25.5 g of fumaric acid in 1,000 ml of methanol, concentrating, cooling and filtering off.

The starting material can be prepared, for example, as follows:

392 g of phosphorus pentoxide are added in the course of about 10 minutes to 3,000 g of chlorosulfonic acid and 835 g of isatoic anhydride are then added in the course of about 60 minutes, the internal temperature being kept at 40° to 60°. The mixture is stirred for a further 120 minutes at 60°, cooled to room temperature and poured carefully onto about 20,000 g of ice, the resulting mixture is stirred for a further 30 minutes and filtered with suction and the material on the filter is washed with five times 1 liter of water and subjected to suction until dry. The 5-chlorosulfonylisatoic anhydride thus obtainable can be subjected to further processing without further purification.

210 g of 5-chlorosulfonylisatoic anhydride are suspended in 780 ml of acetone. 50 g of methylamine are passed into the suspension in the course of about 50 minutes, the internal temperature being kept at 0° to 5° by extensive cooling. The mixture is stirred for a further 3 hours at 0° to 5°, the acetone is substantially stripped off under reduced pressure, 1,500 ml of water are added, with stirring and cooling, the mixture is filtered with suction and the material on the filter is washed with water and suspended in 500 ml of ethanol, the suspension is again filtered with suction and the product is dried under reduced pressure. This yields 5-methylsulfamoylisatoic anhydride with a melting point of 233°–234°. Recrystallisation from tetrahydrofuran raises the melting point to 246°–247°.

EXAMPLE 9

In a manner analogous to that described in Example 8, the reaction of 18.3 g of 5-methylsulfamoylisatoic anhydride with 12.5 g of 1-benzylpiperazine and chromatography on silica gel with chloroform/acetone (95:5–9:1) followed by reaction of the 5-(N-methylsulfamoyl)-anthranilic acid (4-benzyl)-piperazide, thus obtainable, with 5.5 g of fumaric acid yields the fumarate of the said piperazide; the fumarate has a melting point of 220° (decomposition).

EXAMPLE 10

9.2 g of 5-(N-methylsulfamoyl)-anthranilic acid (4-benzyl)-piperazide are dissolved in 100 ml of ethanol, the solution is acidified with 21.6 ml of ethanolic hydrochloric acid, 1 g of palladium (5% on charcoal) is added and the mixture is hydrogenated at room temperature and normal pressure. After filtering off the catalyst and evaporating the filtrate, the hydrochloride of 5-(N-methylsulfamoyl)-anthranilic acid piperazide (melting point 169°) is obtained.

EXAMPLE 11

Tablets containing 25 mg of active ingredient, for example 1-[5-methylsulfamoyl)-anthraniloyl]-4-[2-(p-chlorophenyl)-ethyl]-piperazine or a salt thereof, can be prepared as follows:

Constituents (for 1,000 tablets)

| | |
|---|---|
| Active ingredient | 25.0 g |
| Lactose | 100.7 g |
| Corn starch | 7.5 g |
| Polyethylene glycol 6000 | 5.0 g |
| Talc | 5.0 g |
| Magnesium stearate | 1.8 g |
| Demineralised water | q.s. |

Preparation

All of the solid ingredients are first forced through a sieve of 0.6 mm mesh width. The active ingredient, the lactose, the talc, the magnesium stearate and half of the starch are then mixed. The other half of the starch is suspended in 40 ml of water and this suspension is added to a boiling solution of the polyethylene glycol in 100 ml of water and the mixture is granulated, with the addition of water if necessary. The granules are dried overnight at 35°, forced through a sieve of 1.2 mm mesh width and compressed to tablets which are concave on both sides and about 6 mm in diameter.

Tablets containing, in each case, 25 mg of one of the other compounds of the formula I named in Examples 1 to 10 can also be prepared analogously.

We claim:

1. An anthranilamide compound of the formula

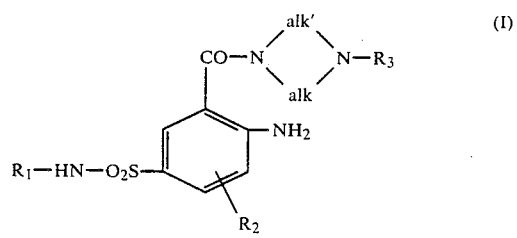

in which $R_1$ is hydrogen, lower alkyl, cycloalkyl having 5 to 8 ring members, bi- or tricycloalkyl, having 5 or 6 ring members in each ring, $R_2$ is hydrogen, lower alkyl, lower alkoxy, halogen or trifluoro-methyl, $R_3$ is hydrogen, lower alkyl, phenyl-lower alkyl or phenyl-lower alkyl substituted in the phenyl moiety by halogen, and alk and alk' are identical or different lower alkylene radicals which separate the nitrogen atoms by 2 or 3 carbon atoms, or a pharmaceutically acceptable salt thereof.

2. A compound as claimed in claim 1, in which $R_1$ is hydrogen, lower alkyl having not more than 4C atoms, cycloalkyl having 5 to 8 ring members, bicyclo- or tricyclo-alkyl having 5 or 6 ring members in each ring, $R_2$ is hydrogen, alk and alk' are ethylene, and $R_3$ is hydrogen, lower alkyl having not more than 4C atoms, or a phenyl-lower alkyl radical which can be substituted in the phenyl moiety by halogen with an atomic number of not more than 35 and has not more than 4C atoms in the lower alkylene moiety, or a pharmaceutically acceptable salt thereof.

3. A compound as claimed in claim 1, in which $R_1$ is lower alkyl having not more than 4C atoms, cycloalkyl having 5 to 8 ring members or tricycloalkyl having 5 or 6 ring members in each ring, $R_2$ is hydrogen, alk and alk' are ethylene and $R_3$ is hydrogen, lower alkyl having not more than 4C atoms or a phenyl-lower alkyl radical which can be substituted in the phenyl moiety by halogen with an atomic number of not more than 35 and has not more than 4C atoms in the lower alkylene moiety, or a pharmaceutically preferable salt thereof.

4. A compound as claimed in claim 1, in which $R_1$ is lower alkyl having not more than 4C atoms, $R_2$ is hydrogen, alk and alk' are ethylene and $R_3$ is hydrogen, lower alkyl having not more than 4C atoms or a phenyl-lower alkyl radical which can be substituted in the phenyl moiety by lower alkyl having not more than 4C atoms, lower alkoxy having not more than 4C atoms and/or halogen, and has not more than 10C atoms, or a pharmaceutically preferable salt thereof.

5. A compound as claimed in claim 1 being 5-(N-Methylsulfamoyl)-anthranilic acid (4-methyl)-piperazide or a pharmaceutically preferable salt thereof.

6. A compound as claimed in claim 1 being 5-(N-Ethylsulfamoyl)-anthranilic acid (4-methyl)-piperazide or a pharmaceutically preferable salt thereof.

7. A compound as claimed in claim 1 being 5-(N-Methylsulfamoyl)-anthranilic acid 4-[2-(p-chlorophenyl)-ethyl]-piperazide or a pharmaceutically preferable salt thereof.

8. A compound as claimed in claim 1 being 5-(N-Methylsulfamoyl)-anthranilic acid (4-benzyl)-piperazide or a pharmaceutically preferable salt thereof.

9. A compound as claimed in claim 1 being 5-(N-Methylsulfamoyl)-anthranilic acid piperazide or a pharmaceutically preferable salt thereof.

10. A pharmaceutical preparation containing an analgetically and/or anti-inflammatorily effective amount of a compound claimed in claim 1 in admixture of conventional pharmaceutical adjuncts and/or carriers.

* * * * *